(12) United States Patent
Lee et al.

(10) Patent No.: US 8,653,267 B2
(45) Date of Patent: Feb. 18, 2014

(54) CO-CRYSTAL COMPOUND OF OPTICAL DEVICE

(75) Inventors: Tu Lee, Flushing, NY (US); Pu-Yun Wang, Fengshan (TW)

(73) Assignee: National Central University, Jhongli (TW)

( * ) Notice: Subject to any disclaimer, the term of this patent is extended or adjusted under 35 U.S.C. 154(b) by 298 days.

(21) Appl. No.: 12/800,209

(22) Filed: May 11, 2010

(65) Prior Publication Data

US 2011/0213148 A1 Sep. 1, 2011

(30) Foreign Application Priority Data

Mar. 1, 2010 (TW) ............................... 99105887 A

(51) Int. Cl.
*C07D 239/02* (2006.01)
(52) U.S. Cl.
USPC ......................................................... 544/317
(58) Field of Classification Search
USPC ......................................................... 544/317
See application file for complete search history.

(56) References Cited

U.S. PATENT DOCUMENTS

| | | | | |
|---|---|---|---|---|
| 5,587,480 | A * | 12/1996 | Belleau et al. | 544/310 |
| 6,228,860 | B1 * | 5/2001 | Mansour et al. | 514/263.23 |
| 2007/0026078 | A1 * | 2/2007 | Almarsson et al. | 424/489 |

FOREIGN PATENT DOCUMENTS

| | | |
|---|---|---|
| WO | WO 9529176 A1 * | 11/1995 |
| WO | WO 2004085432 A1 * | 10/2004 |

OTHER PUBLICATIONS

K. Bouchouit et al., Acta Crystallographica, Section E: Structure Reports Online, E61(8), o2755-o2757 (2005).*
S. Balasubramanian et al., Acta Crystallographica, Section C: Crystal Structure Communications, C64(10), o566-o569 (2008).*
T. Lee et al., 10 Crystal Growth & Design 1419-1434 (Published on Web Jan. 22, 2010).*
Oxford English Dictionary, (Jun. 2004; online version Dec. 2011).*
A Dictionary of Physics (Oxford University Press, 2009).*
P. Tobat et al., Chemical Reviews, 1011-1065 (2007).*

* cited by examiner

*Primary Examiner* — James O Wilson
*Assistant Examiner* — Alexander R Pagano
(74) *Attorney, Agent, or Firm* — Hudak, Shunk & Farine Co. LPA

(57) ABSTRACT

The present invention discloses a co-crystal compound of optical devices. The co-crystal compound is crystallized out with hydrogen bonding by a temperature fluctuation method after mixing small organic molecules without optoelectronic properties and organic molecules having heterocyclic rings with optoelectronic properties. The photoluminescence (PL) intensity of this hydrogen-bonded co-crystal compound according to the present invention can vary with a variety of the small organic molecules without optoelectronic properties, so as to modulate the PL intensity.

2 Claims, 14 Drawing Sheets

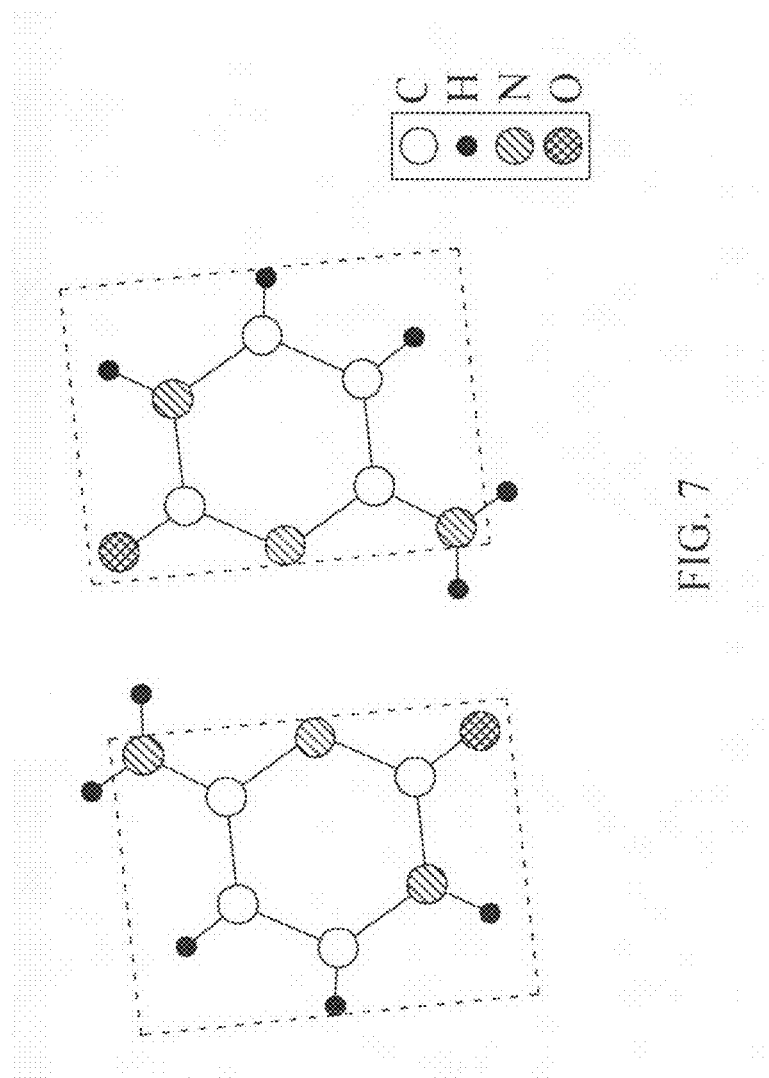

CO-CRYSTAL COMPOUND OF OPTICAL DEVICE

FIELD OF THE INVENTION

The present invention relates to a co-crystal compound, and in particular to a co-crystal compound of optical devices.

BACKGROUND OF THE INVENTION

A co-crystal compound can be obtained by following steps. After the self-assembly of solutes, the temperature of a saturated solution at a high temperature state is lowered to become a supersaturated solution due to different solubilities in different temperatures, such that a crystalline solid is crystallized out gradually from the solute in the solution. Such a crystalline solid is the co-crystal compound. In the process of crystallization, the physical properties of compounds are changed. This technology can provide more diversified development of traditional pharmaceutical industry. For example, solubility, bioavailability, and stability can be increased by using changing the crystalline morphology of the compounds. Formerly, most of those who study the physical and chemical properties of the co-crystal compound are from the pharmaceutical industry, and thus there is no literature making mention of the effect of the co-crystal compound of organic molecules on optical properties. It is only known that solvate prepared by a crystallization process has an extremely influence on the photoluminescence (PL) intensity, there is no report about the influence of the co-crystal compound on the PL intensity.

After a material is excited by light, its inner electrons will be present in an excited state, and then after these electrons return back to a low-energy level, redundant energy will be emitted in a form of light. Such a phenomenon is called as photoluminescence (PL) which can be used to detect the electrical structure of materials. These PL materials are also widely applied in the manufacturing process of organic light-emitting diodes (OLED), or even biologic light-emitting diodes (BioLED). The OLED is made of electron transport materials, hole transport materials and organic luminescent materials, and the organic luminescent materials will determine the luminescent color of devices. A guest material in these organic luminescent materials usually has a higher luminescent efficiency. After mixing into a host material, the guest material receives and combines with excitons from the host material so as to enhance the luminescent efficiency. Although the OLED has the properties of low energy consumption and self-luminescent, it is still desired to improve the luminescent efficiency of the organic luminescent materials and life time thereof.

SUMMARY OF THE INVENTION

In view of the aforementioned drawbacks, an object of the present invention is to provide a co-crystal compound of optical devices in which the photoluminescence (PL) intensity of the co-crystal compound having optoelectronic properties can be adjusted by varying the kinds of small organic molecules without optoelectronic properties. Therefore, the present invention can be applied to, for example, the development of luminescent materials in the manufacturing process of organic light-emitting diodes, or even biologic light-emitting diodes.

According to the object of the present invention, a co-crystal compound of optical devices is provided, comprising organic molecules having heterocyclic rings with optoelectronic properties and small organic molecules without optoelectronic properties mixed in a predetermined ratio. A hydrogen-bonded co-crystal compound having optoelectronic properties is crystallized out by a temperature fluctuation method after mixing the small organic molecules without optoelectronic properties and the organic molecules having heterocyclic rings with optoelectronic properties.

Wherein, in order to avoid production of a salt made from the organic molecules having heterocyclic rings with optoelectronic properties and the small organic molecules without optoelectronic properties in the process of crystallization by means of temperature fluctuations, a difference between dissociation constants ($pK_a$) of the said both organic molecules and small organic molecules may be about less than three. The organic molecules having heterocyclic rings with optoelectronic properties and the small organic molecules without optoelectronic properties may be mixed in a molar ratio of from about 1:1 to about 4:1. Among them, the organic molecules having heterocyclic ring may be purine biomolecules or pyrimidine biomolecules, such as cytosine, and the small organic molecules without optoelectronic properties used may be dicarboxylic acids, such as oxalic acid dihydrate, malonic acid, succinic acid, etc.

The co-crystal compound of optical devices according to the present invention may have one or more advantages as follows:

(1) The PL value of the co-crystal compound according to the present invention can be varied with the kinds of the small organic molecules without optoelectronic properties so as to change the PL intensity thereof. This is not disclosed in the prior art.

(2) The present invention changes the optical properties of organic compounds by the concept of the co-crystal compound. Manufacturing processes in the optoelectronic or semiconductor industry can be simplified through application of the present invention. For example, when there is much need to look for or develop a new material for improving the manufacturing process or solving a problem in the manufacturing process, this technology according to the present invention can be used to optimize and control the properties of the organic compound so as to achieve the required purpose and save time.

BRIEF DESCRIPTION OF THE DRAWINGS

The exemplary embodiments of the present invention will be understood more fully from the detailed description given below and from the accompanying drawings of various embodiments of the invention, which, however, should not be taken to limit the invention to the specific embodiments, but are for explanation and understanding only.

FIG. 7 illustrates a stereogram of the molecular structure of cytosine dimmer in accordance with the present invention.

DETAILED DESCRIPTION OF THE INVENTION

Exemplary embodiments of the present invention are described herein in the context of a co-crystal compound of optical devices.

A co-crystal compound of optical devices is provided according to the present invention. The co-crystal compound comprises organic molecules having heterocyclic rings with optoelectronic properties and small organic molecules without optoelectronic properties, and is crystallized out with hydrogen bonding by a temperature fluctuation method. Moreover, the co-crystal compound has optoelectronic properties and thus can be applied to optical devices, such as the organic film of organic light-emitting diodes, or even biologic light-emitting diodes.

Herein, a difference between dissociation constants ($pK_a$) of the organic molecules having heterocyclic rings with optoelectronic properties and the small organic molecules without optoelectronic properties is about less than three for preventing a salt from production. The organic molecules having heterocyclic rings with optoelectronic properties and the small organic molecules without optoelectronic properties are mixed in a predetermined ratio. The predetermined ratio may be in a molar ratio of from about 1:1 to about 4:1. The organic molecules having heterocyclic ring with optoelectronic properties may comprise purine biomolecules or pyrimidine biomolecules, such as cytosine, and the dissociation constant of cytosine is about 4.5. The selected small organic molecules without optoelectronic properties may comprise dicarboxylic acids, such as oxalic acid dihydrate, malonic acid, and succinic acid. The first and second dissociation constants of oxalic acid dihydrate are 1.0 and 3.7, respectively. The first and second dissociation constants of malonic acid are 2.6 and 5.1, respectively. The first and second dissociation constants of succinic acid are 4.0 and 5.1, respectively.

Moreover, the difference of kinds of the small organic molecules can result in the increase or decrease of the photoluminescence (PL) intensity of the co-crystal compound according to the present invention. Therefore, the PL intensity of the small organic molecules without optoelectronic properties can be adjusted by means of changing their kinds.

Figure 1:
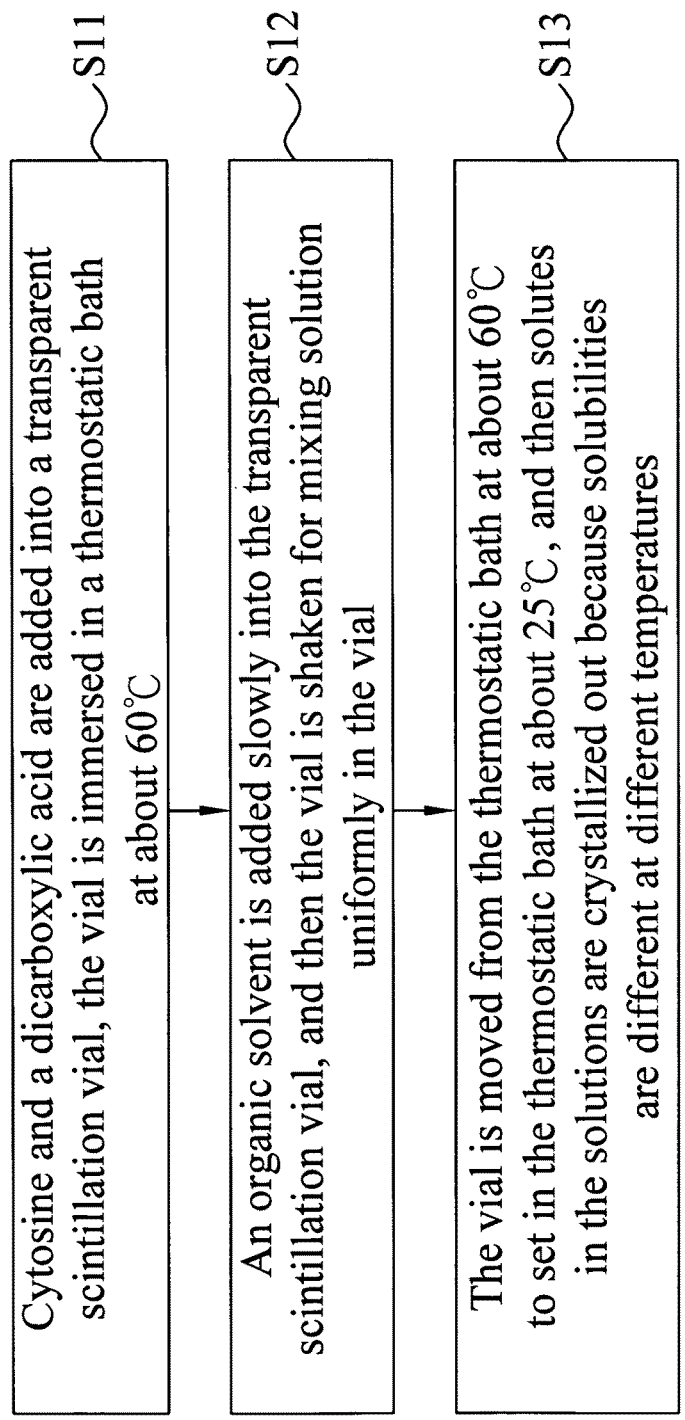
FIG. 1 illustrates a flowchart of manufacturing a co-crystal compound in accordance with the present invention.
Figure 2:
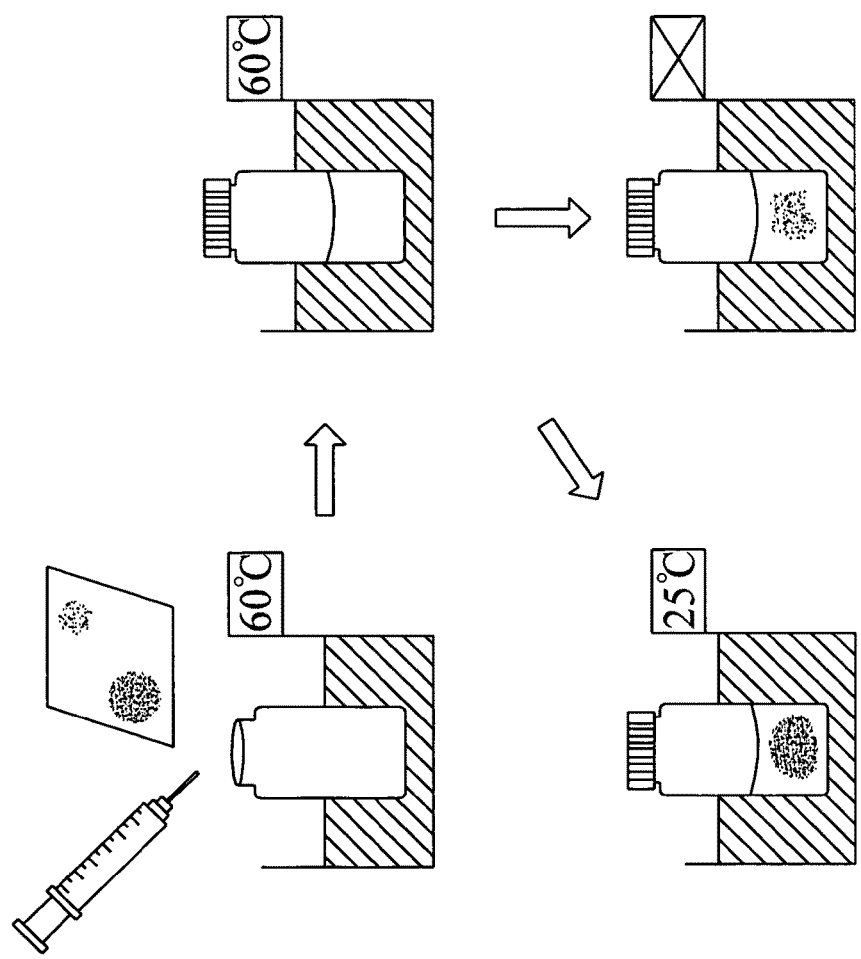
FIG. 2 illustrates a schematic diagram of manufacturing the co-crystal compound in accordance with the present invention.
Figure 3A:
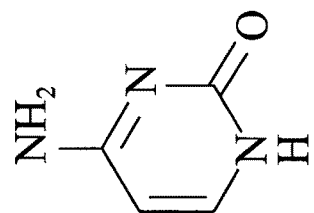
FIG. 3A illustrates a molecular structure of cytosine.
Figure 3B:
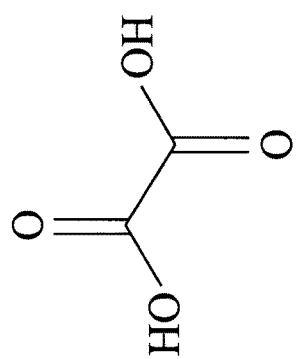
FIG. 3B illustrates a molecular structure of oxalic acid.
Figure 3C:
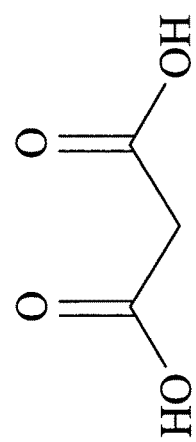
FIG. 3C illustrates a molecular structure of malonic acid.
Figure 3D:
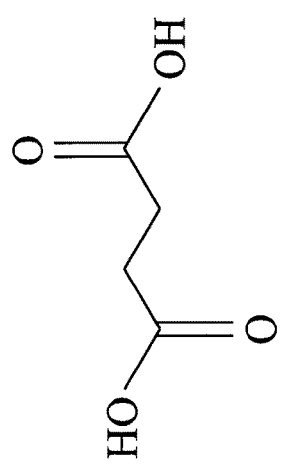
FIG. 3D illustrates a molecular structure of succinic acid.

Please refer to FIGS. 1 and 2, respectively, for a flowchart and a schematic diagram of manufacturing a co-crystal compound in accordance with the present invention. In this embodiment, cytosine is taken as an example of the organic molecules having heterocyclic rings with optoelectronic properties, and oxalic acid dihydrate, malonic acid and succinic acid are used as examples of the small organic molecules without optoelectronic properties. As shown in FIG. 1, the steps of manufacturing a co-crystal compound comprise as follows. In step 11, oxalic acid dihydrate (with oxalic acid structure as shown in FIG. 3B), malonic acid (with structure as shown in FIG. 3C) and succinic acid (with structure as shown in FIG. 3D) are, respectively, added into transparent scintillation vials with cytosine (with structure as shown in FIG. 3A) in a molar ratio of about 2:1. Thus, there are totally three scintillation vials which contain cytosine and oxalic acid dihydrate, cytosine and malonic acid, and cytosine and succinic acid, respectively. The temperature of the thermostatic bath is set at about 60° C., and then these vials are immersed in the thermostatic bath so as to heat indirectly the mixture in these vials. In step 12, each vial is opened but is still immersed in the thermostatic bath. Organic solvents, which are capable of dissolving the above-mentioned cytosine, oxalic acid dihydrate, malonic acid, and succinic acid, are slowly added into the each vial using a micropipette, and meanwhile, the vials are shaken to mix solutions uniformly in the vials and accelerate the dissolution. In step 13, the solvents are continuously added into the vials till cytosine, oxalic acid dihydrate, malonic acid, and succinic acid as solutes are completely dissolved and the solution are clear and saturated. After that, the saturated solutions in the vials are moved from the thermostatic bath at about 60° C. to set in the thermostatic bath at about 25° C. Due to solubility being varied with different temperatures, the saturated solutions in a high temperature state will become supersaturated solutions after lowering the temperature, such that solutes in the solutions are crystallized out gradually in solid form in the vials, finally obtaining co-crystal compounds of the present invention.

Figure 4A:
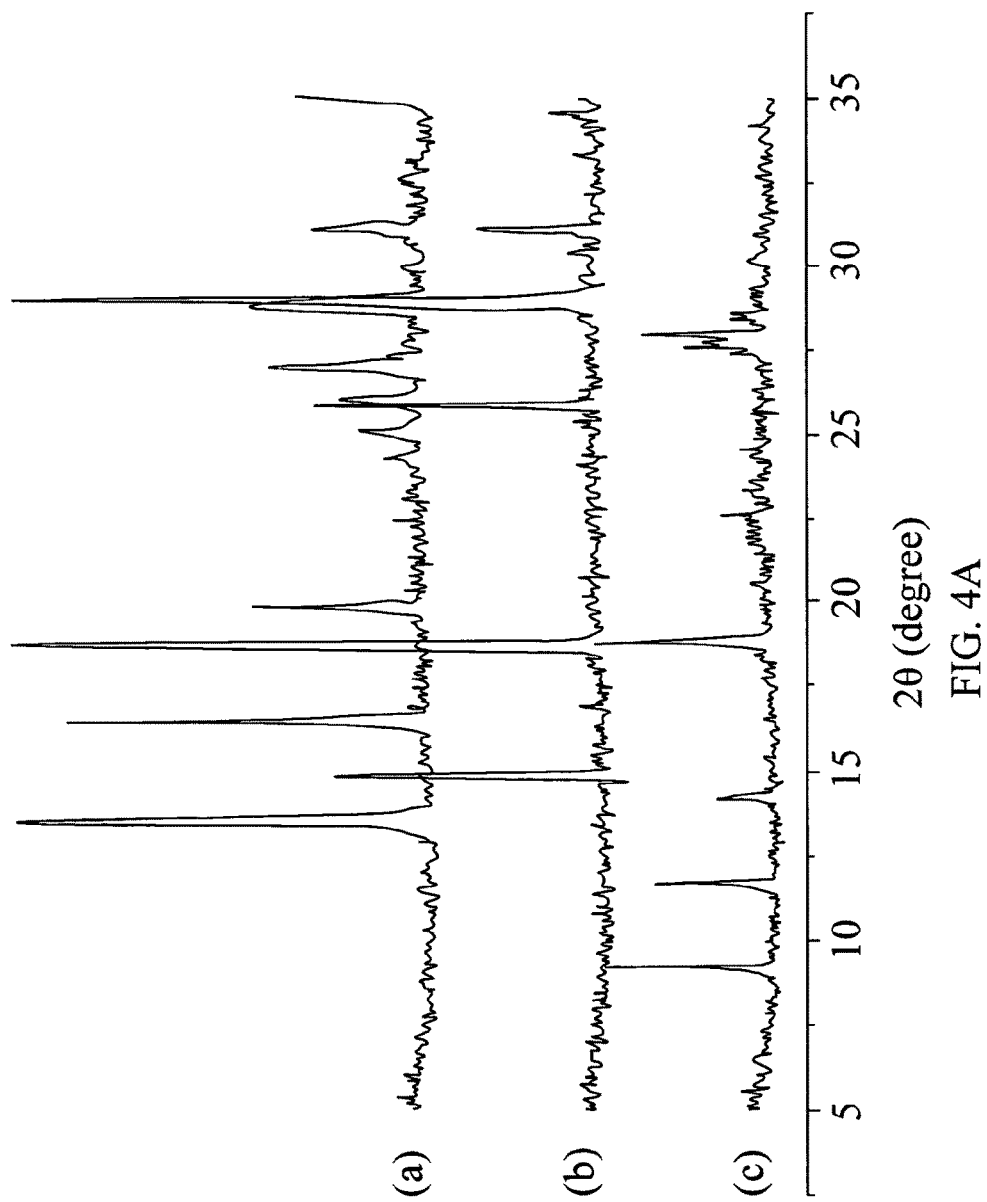
FIG. 4A illustrates PXRD patterns of (a) cytosine, (b) oxalic acid dihydrate, and (c) a co-crystal compound made from cytosine and oxalic acid dihydrate in accordance with the present invention.
Figure 4B:
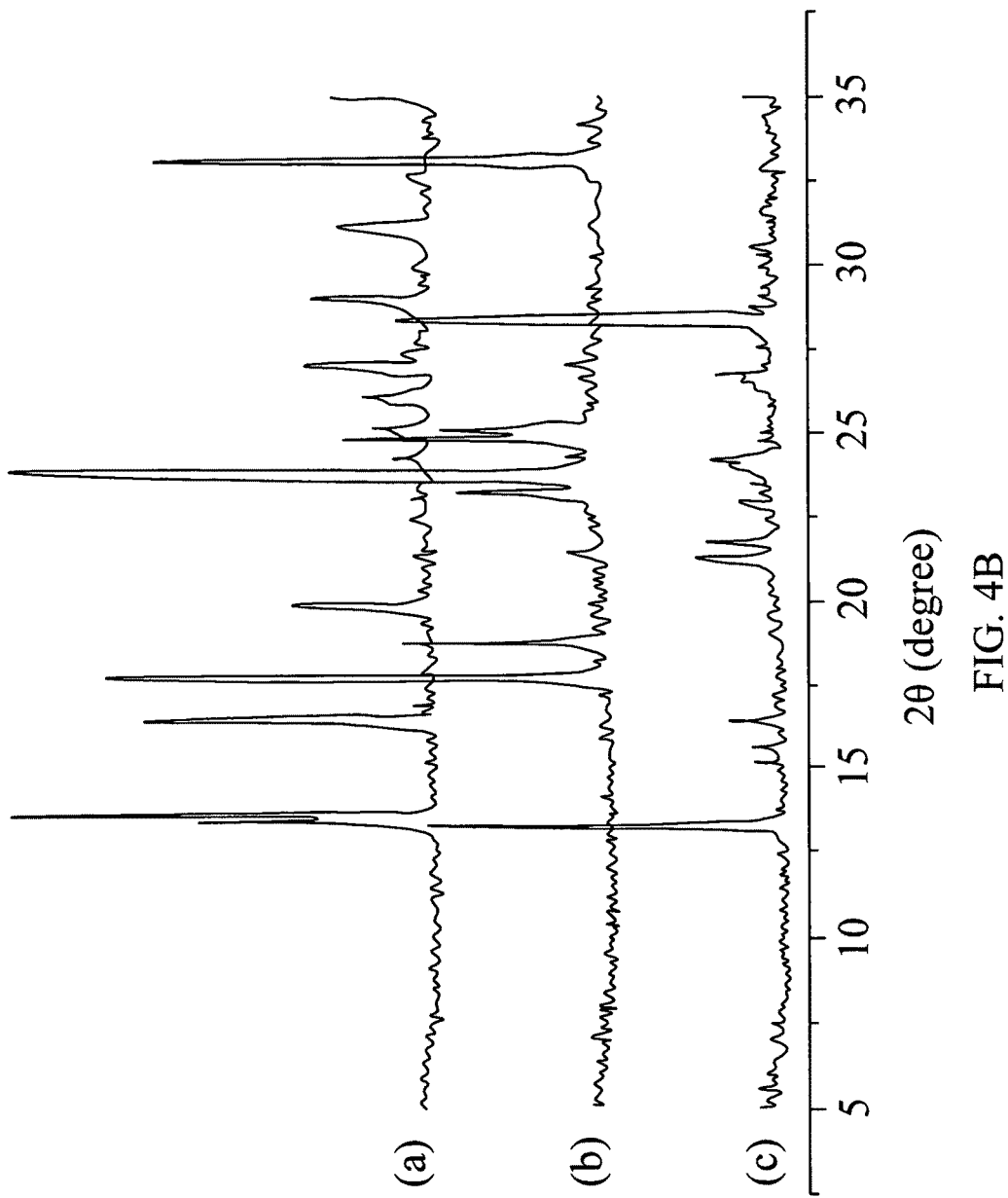
FIG. 4B illustrates PXRD patterns of (a) cytosine, (b) malonic acid, and (c) a co-crystal compound made from cytosine and malonic acid in accordance with the present invention.
Figure 4C:
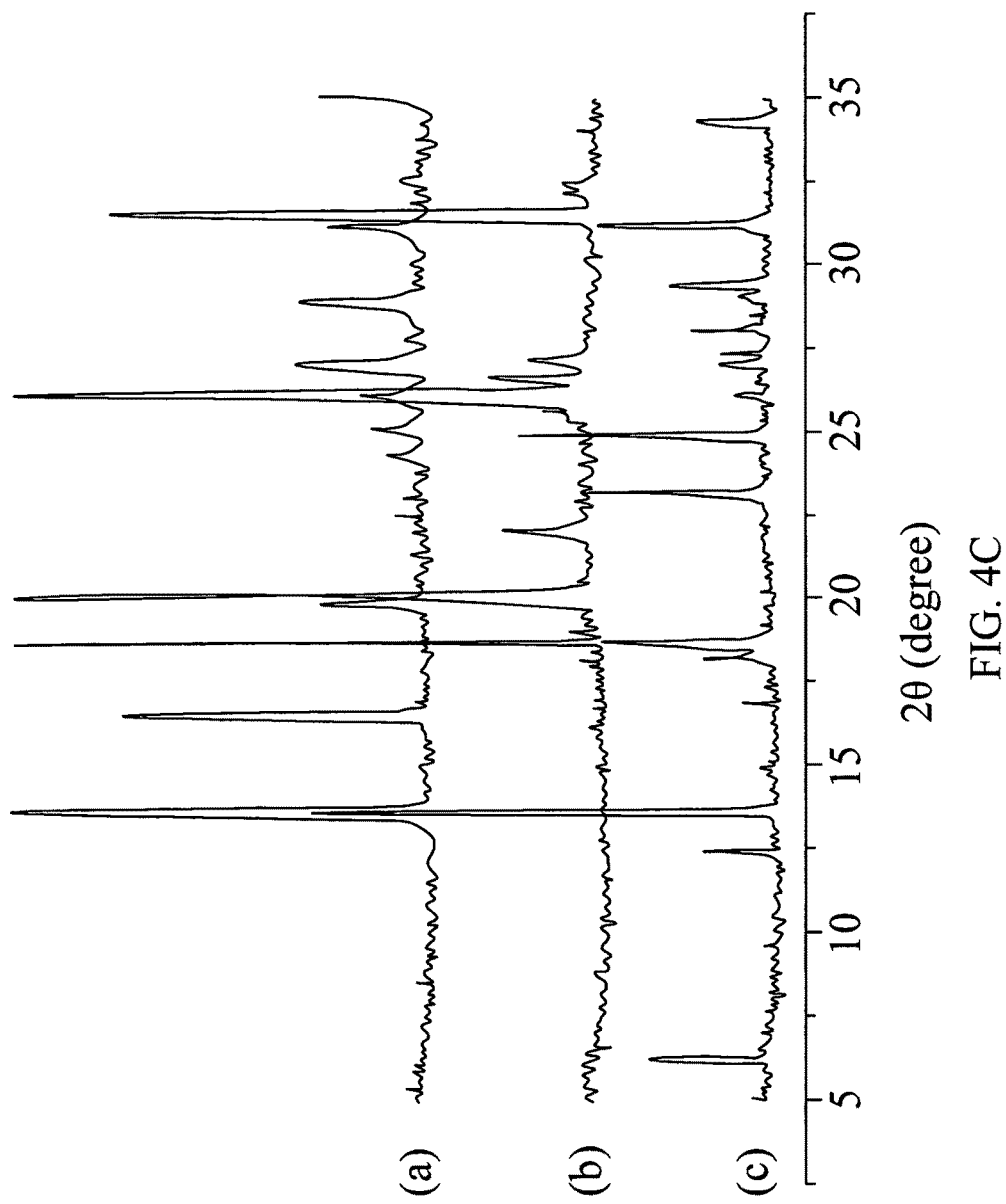
FIG. 4C illustrates PXRD patterns of (a) cytosine, (b) succinic acid, and (c) a co-crystal compound made from cytosine and succinic acid in accordance with the present invention.
Figure 5A:
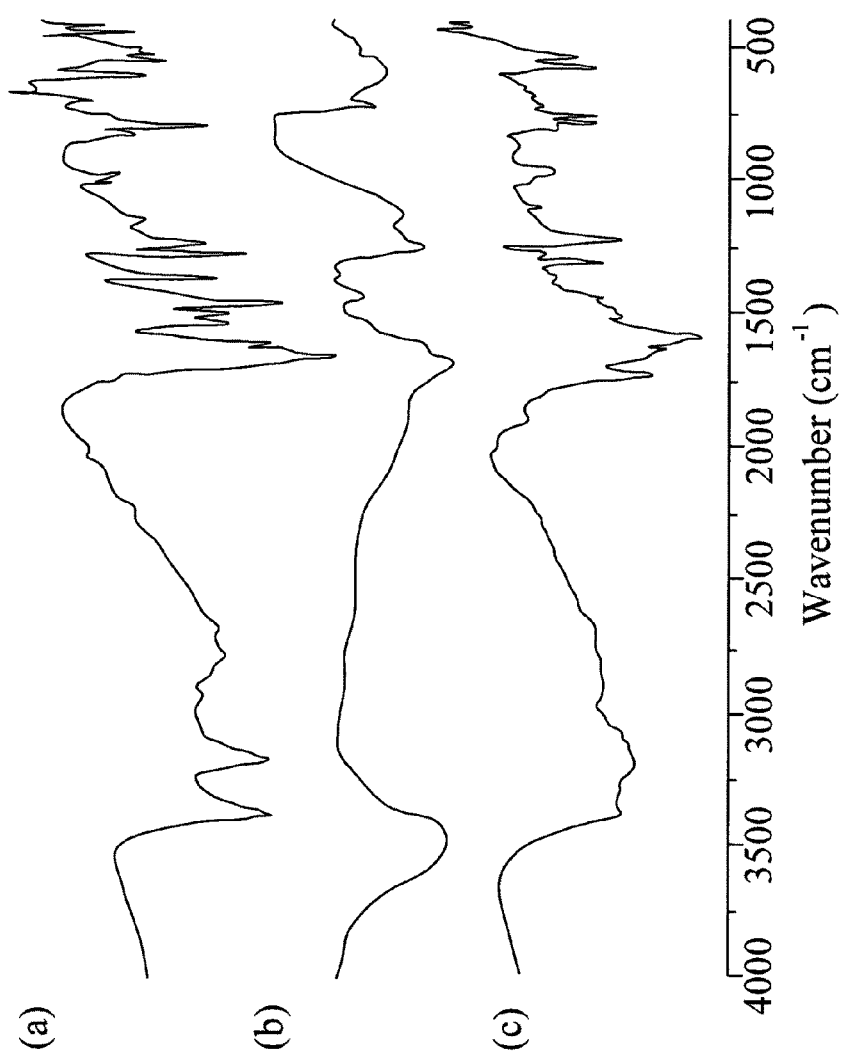
FIG. 5A illustrates FT-IR spectra of (a) cytosine, (b) oxalic acid dihydrate, and (c) a co-crystal compound made from cytosine and oxalic acid dihydrate in accordance with the present invention.
Figure 5B:
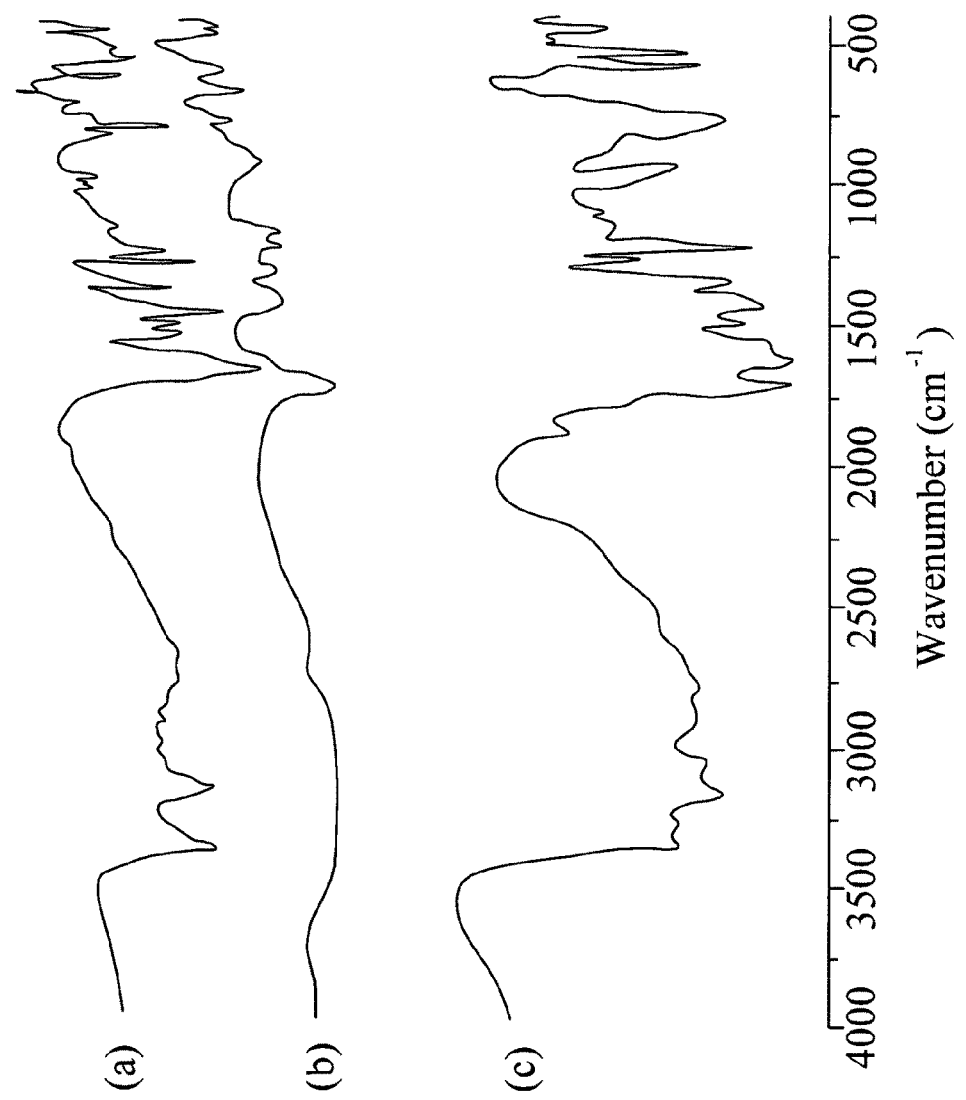
FIG. 5B illustrates FT-IR spectra of (a) cytosine, (b) malonic acid, and (c) a co-crystal compound made from cytosine and malonic acid in accordance with the present invention.
Figure 5C:
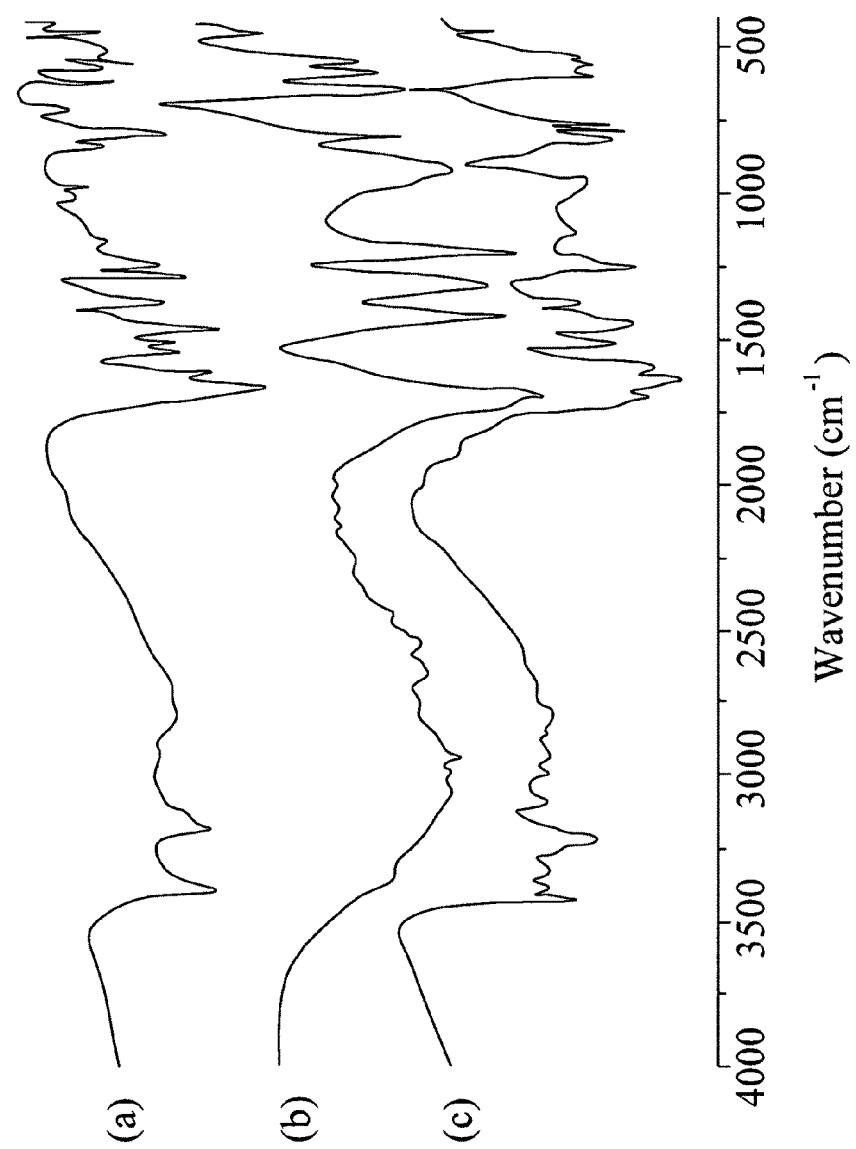
FIG. 5C illustrates FT-IR spectra of (a) cytosine, (b) succinic acid, and (c) a co-crystal compound made from cytosine and succinic acid in accordance with the present invention.

If there is need to take a long single crystal for single crystal X-ray diffraction measurement, alternatively, the temperature controlling system of the thermostatic bath is turned off after dissolving entirely the solutes in the vials so as to lower slowly the temperature to room temperature. By this method, the co-crystal compound according to the present invention can be also obtained. Besides, a powder X-ray diffraction (PXRD) analyzer and a Fourier transform infrared spectrum (FT-IR) analyzer can be used to detect crystals precipitated in the each vial for confirming whether all the precipitated crystals are the crystal of the co-crystal compounds or not. Cytosine, oxalic acid dihydrate, and a co-crystal compound made from cytosine and oxalic acid dihydrate by the temperature fluctuation method are analyzed by the PXRD analyzer, and the analyzed results of (a) cytosine, (b) oxalic acid dihydrate, and (c) the co-crystal compound thereof are shown in the FIG. 4A. Through the analysis of the PXRD analyzer, the analyzed results of (a) cytosine, (b) malonic acid, and (c) a co-crystal compound made from cytosine and malonic acid by the temperature fluctuation method are shown in the FIG. 4B, and the analyzed results of (a) cytosine, (b) succinic acid, and (c) a co-crystal compound made from cytosine and succinic acid by the temperature fluctuation method are shown in the FIG. 4C. Moreover, through the analysis of the FT-IR analyzer, the analyzed results of (a) cytosine, (b) oxalic acid dihydrate, and (c) the co-crystal compound thereof are shown in the FIG. 5A; the analyzed results of (a) cytosine, (b) malonic acid, and (c) the co-crystal compound thereof are shown in the FIG. 5B; and the analyzed results of (a) cytosine, (b) succinic acid, and (c) the co-crystal compound thereof are shown in the FIG. 5C. In sum, it is confirmed that the co-crystal compounds indeed exist in the crystalline solid precipitated in the each vial.

In addition, for the crystals having better quality and larger size in the each vial, the molecular structure thereof are analyzed by a single crystal X-ray diffraction so as to obtain stoichiometry and molecular formula of the co-crystal compounds made from cytosine and, respectively, the three different small organic molecules without optoelectronic properties, as shown in Table I. The molecular formula of cytosine is $C_4H_5ON_3$. The molecular formulas of the oxalic acid dihydrate, malonic acid, and succinic acid are respectively $C_2H_6O_6$, $C_3H_4O_4$, and $C_4H_6O_4$, and the molecular formulas of the co-crystal compounds of the said three organic molecules mixed with cytosine separately are $C_{18}H_{26}O_{10}N_{12}$, $C_{11}H_{14}O_6N_6$, and $C_{12}H_{16}O_6N$, respectively.

TABLE I

| Co-crystal compounds | Stoichiometry |
|---|---|
| Co-crystal compound of cytosine and oxalic acid dihydrate | $4 \times (C_4H_5ON_3) + 1 \times C_2H_6O_6 = C_{18}H_{26}O_{10}N_{12}$ |
| Co-crystal compound of cytosine and malonic acid | $2 \times (C_4H_5ON_3) + 1 \times C_3H_4O_4 = C_{11}H_{14}O_6N_6$ |
| Co-crystal compound of cytosine and succinic acid | $2 \times (C_4H_5ON_3) + 1 \times C_4H_6O_4 = C_{12}H_{16}O_6N_6$ |

Figure 6:
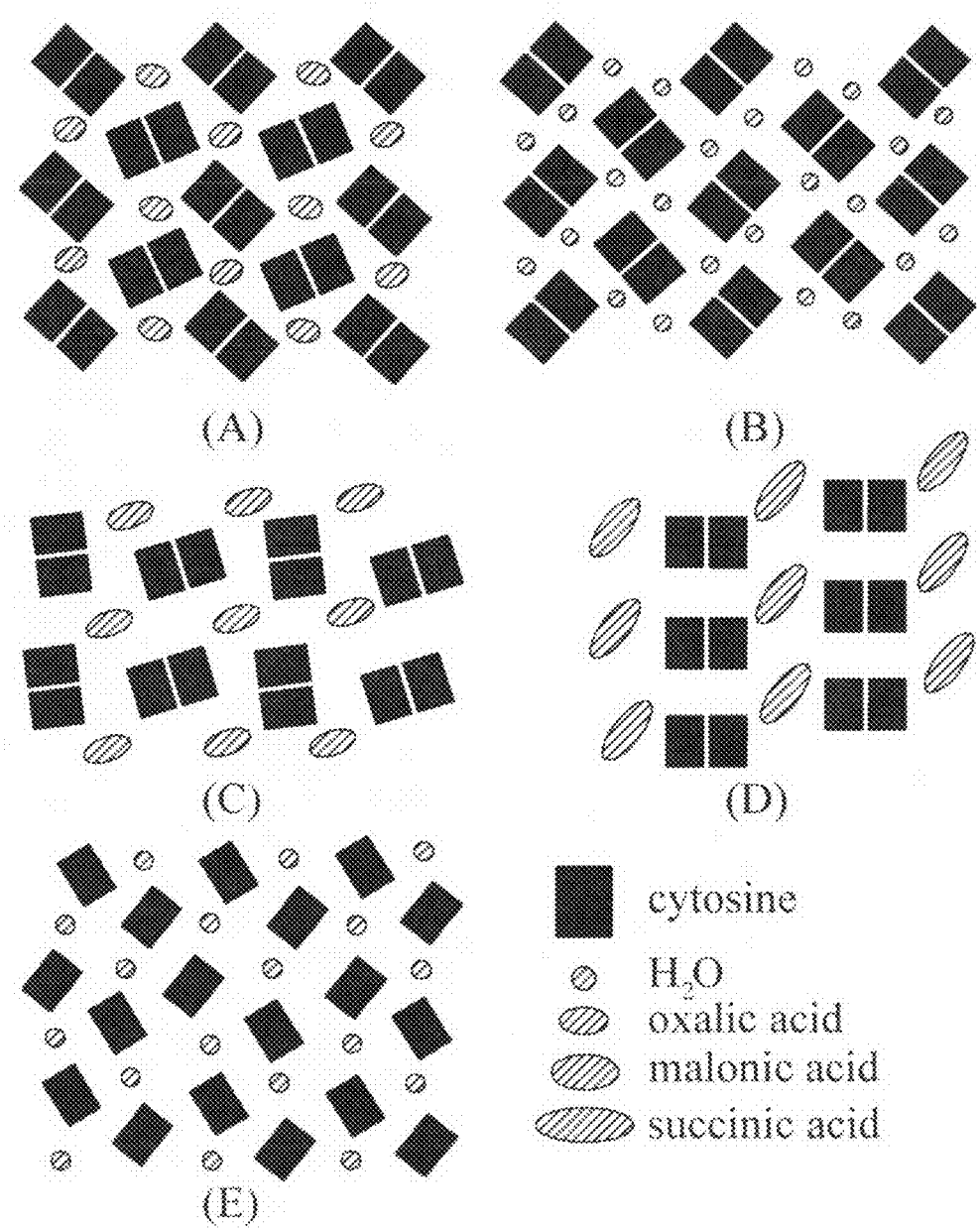
FIG. 6 illustrates (A) a schematic diagram of the molecular structure of the co-crystal compound made from cytosine and oxalic acid dihydrate; (B) a schematic diagram of the molecular structure of the co-crystal compound made from cytosine and oxalic acid dihydrate comprising water molecules; (C) a schematic diagram of the molecular structure of the co-crystal compound made from cytosine and malonic acid; (D) a schematic diagram of the molecular structure of the co-crystal compound made from cytosine and succinic acid; and (E) a schematic diagram of cytosine hydrate in accordance with the present invention.

Please refer to FIG. 6, wherein FIG. 6(A) shows a schematic diagram of the molecular structure of the co-crystal compound of cytosine and oxalic acid dihydrate; FIG. 6(B) shows a schematic diagram of the molecular structure of the co-crystal compound of cytosine and oxalic acid dihydrate comprising water molecules; FIG. 6(C) shows a schematic diagram of the molecular structure of the co-crystal compound of cytosine and malonic acid; FIG. 6(D) shows a schematic diagram of the molecular structure of the co-crystal compound of cytosine and succinic acid; and FIG. 6(E) shows a schematic diagram of cytosine hydrate in accordance with the present invention. After observing the molecular structure of each the co-crystal compound, it is found that cytosine can also form by itself a dimer without proton transfer due to the influence of dicarboxylic acids. The dimmer has a molecular recognition character, as shown in FIG. 7, so as to help understand the functions and regulation mechanism of biological molecules.

In order to observe the changes of the optoelectronic properties of these three co-crystal compounds, a fluorescence spectroscopy is used to measure PL spectra thereof. It is found that the PL intensity has obviously changes. The PL intensity of the co-crystal compound of cytosine and malonic acid is 1-2 times larger than the PL intensity of only cytosine, but the PL intensities of the co-crystal compounds of cytosine and, respectively, oxalic acid dihydrate and succinic acid decrease. The excitation wavelength, emission wavelength, and PL intensity of the each co-crystal compound are shown in Table II.

TABLE II

| Samples | Excitation wavelength (nm) | Emission wavelength (nm) | PL intensity (a.u.) |
|---|---|---|---|
| Cystosine | 345 | 392 | 450 |
| Co-crystal compound of cytosine and oxalic acid dihydrate | 345 | 392 | 212 |
| Co-crystal compound of cytosine and malonic acid | 345 | 392 | 625 |
| Co-crystal compound of cytosine and succinic acid | 345 | 392 | 281 |

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiments of the present invention.

What is claimed is:

1. A co-crystal compound, comprising:
cytosine and oxalic acid dihydrate, wherein the co-crystal compound is prepared by mixing the cytosine and the oxalic acid dihydrate and crystallizing out the co-crystal compound; and
wherein a molecular formula of the co-crystal compound is $C_{18}H_{26}O_{10}N_{12}$.

2. The co-crystal compound of claim 1, wherein the cytosine and the oxalic acid dihydrate is mixed in a molar ratio of about 4:1.

* * * * *